US006806214B2

United States Patent
Li et al.

(10) Patent No.: US 6,806,214 B2
(45) Date of Patent: Oct. 19, 2004

(54) COMPOSITE TEXTILE MATERIAL

(75) Inventors: Yi Li, Kowloon (HK); Kwok Wing Yeung, Kowloon (HK); Yi Lin Kwok, Kowloon (HK); Weilin Xu, Kowloon (HK)

(73) Assignee: The Hong Kong Polytechnic University, Kowloon (HK)

( * ) Notice: Subject to any disclaimer, the term of this patent is extended or adjusted under 35 U.S.C. 154(b) by 278 days.

(21) Appl. No.: 09/759,241

(22) Filed: Jan. 16, 2001

(65) Prior Publication Data

US 2002/0094740 A1 Jul. 18, 2002

(51) Int. Cl.[7] .................. D03D 15/00; B32B 27/12
(52) U.S. Cl. .................. 442/213; 442/394; 442/381; 442/385
(58) Field of Search ................ 442/394, 381, 442/385

(56) References Cited

U.S. PATENT DOCUMENTS 5,185,011 A * 2/1993 Strasser ...................... 604/385
5,735,145 A * 4/1998 Pernick ......................... 66/196
6,436,081 B1 * 8/2002 Wada et al. ............. 604/385.01
2002/0064639 A1 * 5/2002 Rearick et al. .......... 428/292.1
2002/0165511 A1 * 11/2002 Bast et al. .................... 604/378

FOREIGN PATENT DOCUMENTS

EP          0496567 A2 *  7/1992  ........... A61F/13/15

* cited by examiner

*Primary Examiner*—Glenn Caldarola
*Assistant Examiner*—Alexis Wachtel
(74) *Attorney, Agent, or Firm*—Leydig, Voit & Mayer, Ltd.

(57) ABSTRACT

A composite textile fabric includes a composite layer of a hydrophobic material and a layer of a hydrophilic material knitted or otherwise formed together. The composite layer has an upper surface of small exposed areas of the hydrophilic material covering a total area about 25% of the overall area of the upper surface. The composite layer provides one way liquid transport for moisture, extending from the upper surface towards a lower surface of the composite layer.

8 Claims, 4 Drawing Sheets

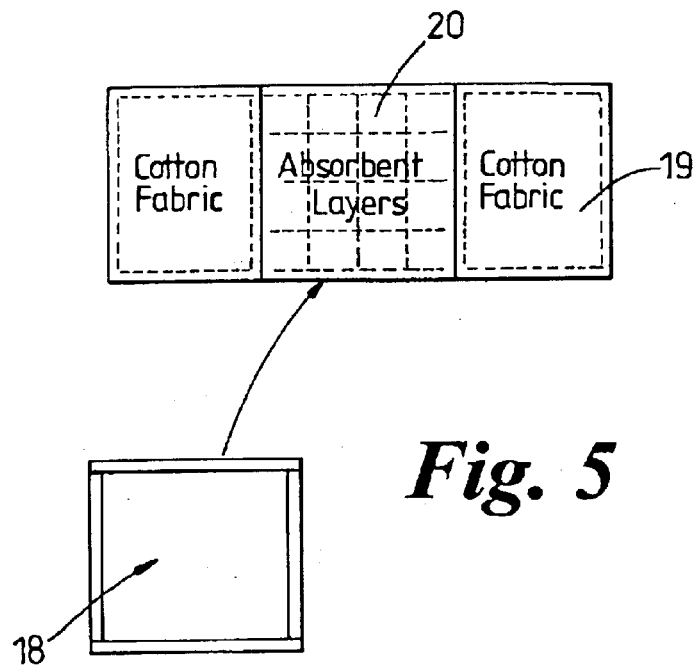
Fig. 5
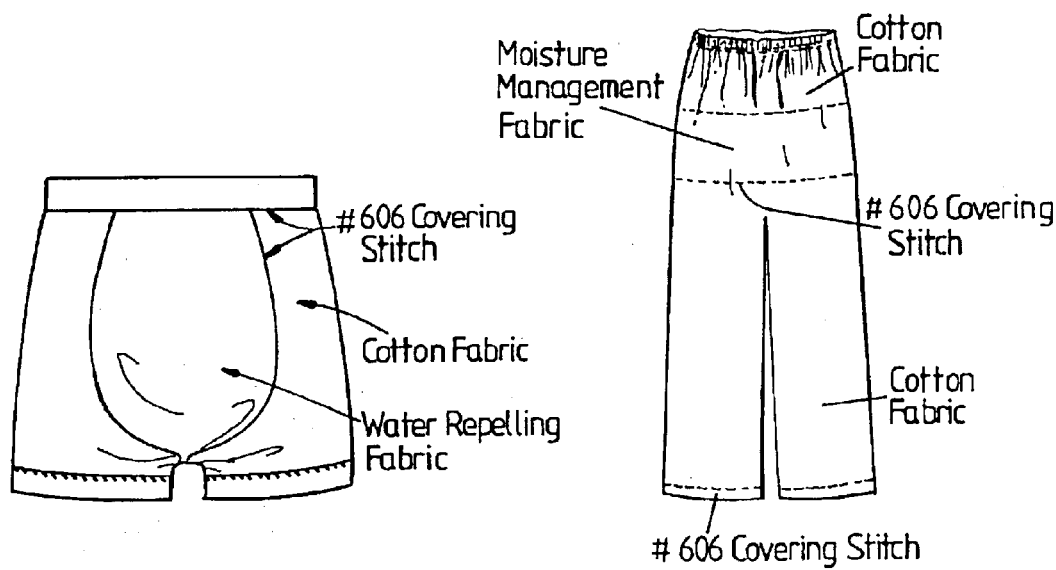
Fig. 6
Fig. 7

COMPOSITE TEXTILE MATERIAL

BACKGROUND OF THE INVENTION

1. Field of the Invention

The invention relates to composite textile materials.

2. Description of Prior Art

The invention relates more particularly to composite textile materials that have applications in moisture management. Basically, there is an on-going requirement to make clothing, especially sports clothing, diapers and incontinence apparel and so forth more comfortable and healthier to wear and use, even though considerable moisture or liquids may be liberated by the wearer in normal use. It is known to provide composite textile materials that comprise distinct layers of materials having respective appropriate characteristics so that moisture, or liquid, migrates or drains quickly away from an inner surface of the material in contact with the body of a wearer. The liquid may be retained in a second outer layer in the case of a diaper or evaporate normally from outer surface of the material where there is only one layer, in the case of sports clothing.

Considerable developments have already taken place in providing suitable materials. However difficulties remain especially with multi-layer materials because they are bulky and uncomfortable or certainly difficult to style fashionably. Also, even though the present materials may keep the wearer's skin relatively dry and comfortable in use at first, once an absorbent layer becomes saturated or relatively wet, the moisture or liquid may migrate back towards the body of the user. Presently used composite materials, especially where they are multi-layer, are usually not re-usable.

SUMMARY OF THE INVENTION

It is an object of the invention to overcome or to at least reduce this problem.

According to the invention there is provided a composite textile fabric for use in moisture management of textiles and garments, the composite fabric comprising a generally uniformly integrated fabric layer with an inner exposed surface that is predominantly hydrophobic material and an outer surface that is predominantly hydrophilic material, whereby the fabric forms a one-way liquid transport system extending away from the inner surface towards the outer surface.

The hydrophobic material may be polypropylene.

The hydrophilic material may be one of polyester and cotton.

A re-usable diaper may have an inner layer of the composite textile fabric, a middle layer of treated cotton fabric, and an outer layer of a water-proof material.

A diaper may have an inner layer of the composite textile fabric, a middle layer of disposable absorbent material, and an outer layer of a waterproof material.

Clothing that may include the composite textile fabric layer may be boxer shorts or long pants.

A mattress cover may include the composite textile fabric layer.

BRIEF DESCRIPTION OF THE DRAWINGS

Composite textile fabric materials and their applications according to the invention will now be described by way of example with reference to the accompanying drawings in which:

FIG. 5 is a plan view of a mattress cover;

FIG. 6 is a front view of boxer shorts;

FIG. 7 is a front view of long parts; and

DESCRIPTION OF THE PREFERRED EMBODIMENTS

Composite textile fabrics and articles made with materials according to the invention comprise a generally uniformly integrated layer that includes a combination of a hydrophobic material and a hydrophilic material. The combination can made by a number of well-practiced techniques including knitting, weaving, and other means, that are used for joining or retaining materials together to form a fabric. In the composite fabric, an inner layer, that normally contacts a body of a user, is predominately a hydrophobic textile material such as polypropylene. In contrast, the outer layer is predominately a hydrophilic material. Typically, the inner surface has, over its inner surface, a number of very small areas of the hydrophilic material that are distributed evenly in the surface of the outer layer. The small areas, when totalled together, make up typically about 25% of the overall area of the inner surface. When the inner surface is wetted, moisture migrates into the composite fabric via paths formed by hydrophilic material and away from the body of the user.

As such, the composite fabric acts as a one-way liquid transport system that takes moisture immediately away from the body of a user and holds the liquid in the hydrophilic material. Due to the physical distribution of the hydrophobic and hydrophilic materials within the fabric, there is no tendency under normal conditions for moisture, or liquid, to migrate towards the body of the user via the hydrophilic material. A further layer of absorbent material may be combined in the composite fabric or placed against the outer surface to increase the volume of liquid that can be retained, or in effect, stored in the fabric or an article, such as a diaper, incorporating the composite material.

It will be appreciated that the small areas of hydrophilic material may comprise a wide range of percentages of the overall exposed inner surface area of the fabric. Whereas 25% is a generally satisfactory and efficient value, the percentage may be considerately higher or lower according to the required use and material or types of those materials that make up the hydrophobic and hydrophilic parts.

Figure 1:
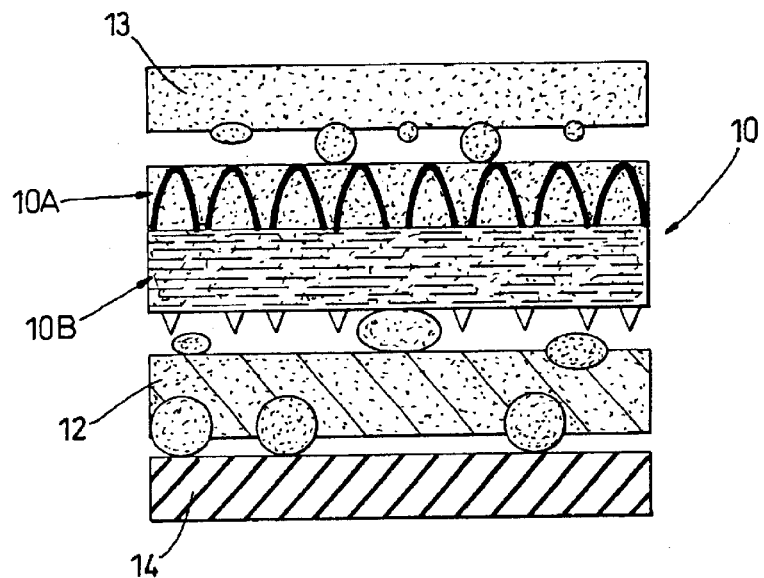
FIG. 1 is diagrammatic representation of a cross section of a diaper incorporating the composite textile material.

Referring to the drawings, in FIG. 1 a typical arrangement of a diaper is shown. The composite material is provided as an inner layer 10 of hydrophobic material 10A and hydrophilic material 10B. In practice, the material 10A is actually uniformly "impregnated" with hydrophilic material 10B by weaving, knitting, or any other techniques, so that an exposed upper surface of the layer 10 comprises small areas of the hydrophilic material. The small areas provide passage or ducts for moisture, or liquids to migrate from the upper surface into the bulk of the hydrophilic material 10B of the composite layer. Because the passages each have a small cross-section and are surrounded by hydrophobic material, the composite layer 10 acts as a one-way liquid transport system. An outer absorbent storage layer 12 is provided to collect water from the bulk of the material 10B and a waterproof layer or cover 14 prevents moisture or water from dispersing out of the diaper in an otherwise conventional manner.

Generally stated, there is no tendency or likelihood of liquid passing towards the exposed upper syrface of the layer 10 material 10B to the material 10A, even under gravity, during use, and so a wearer's skin normally remains dry.

The layer 10 is re-usable (i.e. washable). For reusable diapers, the layer 12 can be also be made of reusable materials. On the other hand, where desired, the layer 12 can be made of disposable material and used only once. In this situation, the layer 12 is preferably separately applied or attached to the layer 10 so that the layer 10 can be reused with a new different layer 12.

In another embodiment, the layer 12 is, in effect, combined with the layer 10, such that when the materials 10A and 10B are knitted or woven together, the layer 12 forms part of the composite layer 10 and is knitted or woven into the layer 10. In that case, the inner surface is predominantly a hydrophobic material with a number small exposed areas of the hydrophilic material.

In any event, the composite layer represents the main departure from the prior art and can be used separately or as part of a diaper, an incontinence bed cover, underpants, or underslips, and so forth. For sportswear, the composite material alone can be made into an article or can be part of an article of clothing. Moisture that migrates into the material 10B will evaporate into the atmosphere in normal use and the skin of the wearer will remain dry and comfortable.

Figure 2:
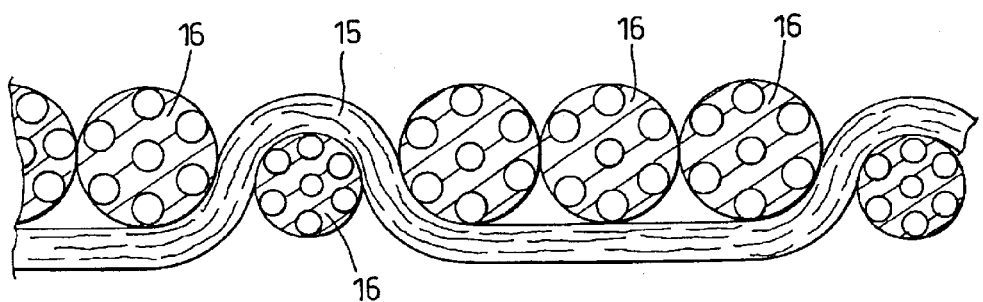
FIG. 2 is an enlarged cross-section of part of the composite material.

In FIG. 2, part of the upper surface of composite material layer 10 is shown. A strand of hydrophilic material 15 is interspaced with strands of hydrophobic material 16 so that the area (overall) of the upper surface is about 25% hydrophilic material. Each downward directed part of the strand 15 shown in the figure represents a narrow passage or duct to transport moisture into the hydrophilic material predominantly constitutes the lower surface of the composite layer.

Figure 3:
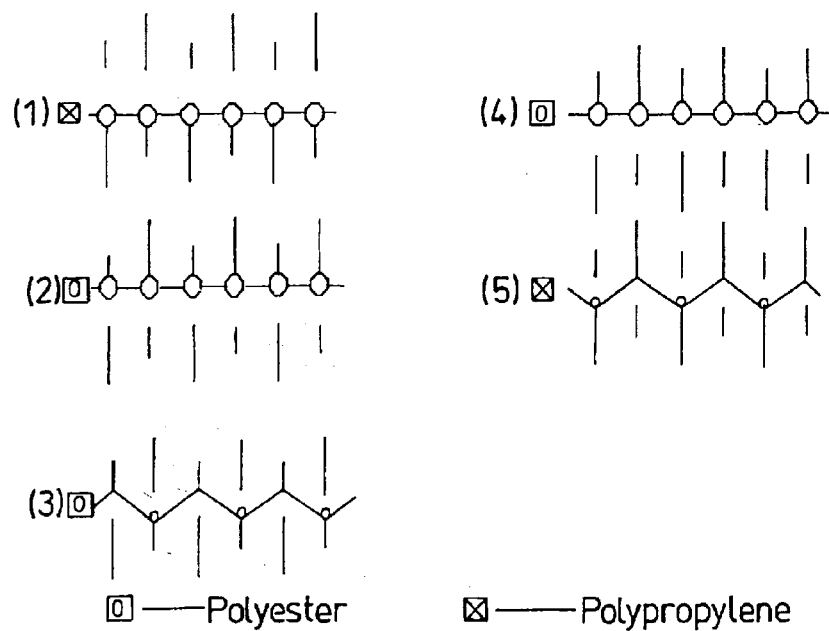
FIG. 3 shows knitting instructions for forming the composite material.

The composite layer is formed by knitting, and a suitable knitting structure is shown in FIG. 3. The composite material is knitted on a multi-function cylinder, dial and two track knitting machine. Two filament yarns are used. The first yarn is a polypropylene filament yarn with a tenacity of 17.4 tex (double yarn of 8.7 tex) and the second yarn is polyester (Coolmax) filament yarn with a tenacity of 8.5 tex.

Figure 4:
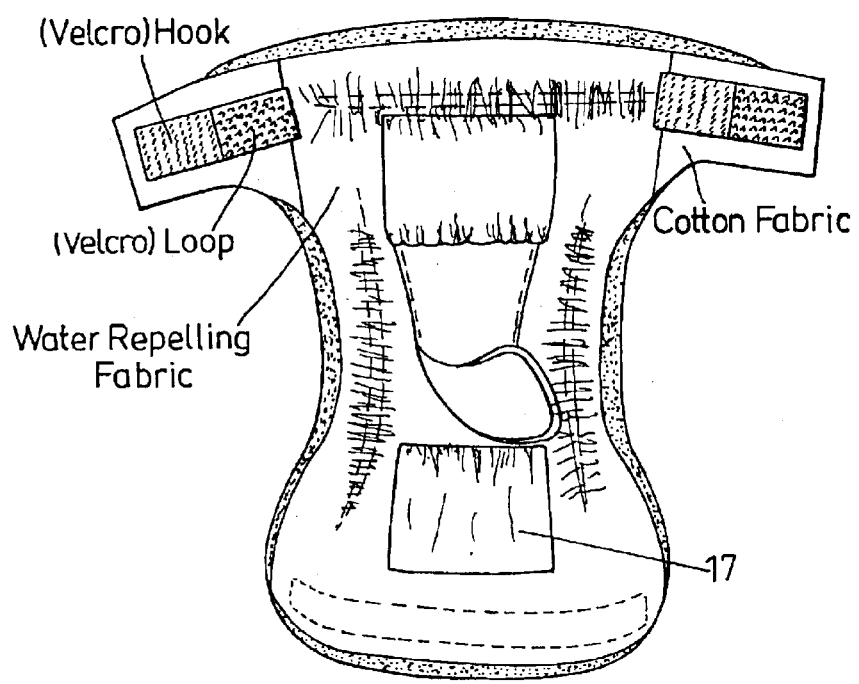
FIG. 4 is a front view of an open diaper.
Figure 8:
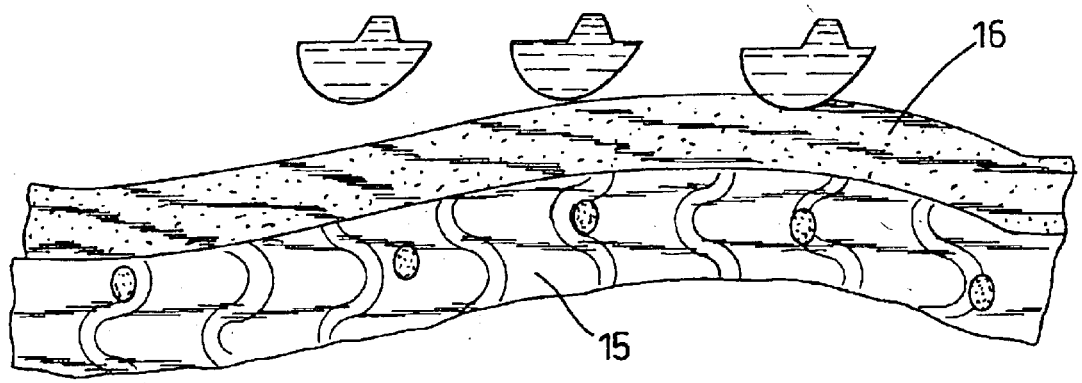
FIG. 8 is different representation of the material of FIG. 2.

In FIG. 4, the diaper is generally conventional but is provided with a layer 17 of the composite material. The layer 17 may be permanently attached to a re-usable diaper or insertable into a suitable pocket for example, 5 for a disposable diaper. The layer 17 itself is reusable.

In FIG. 5, a removable layer 18 of composite material is arranged to fit into or centrally over an incontinence draw sheet or mattress cover formed otherwise of cotton fabric 19 with a central absorbent layer 20.

The composite material may also be used in a similar manner, preferably as an insertable layer in clothing, such as boxer shorts shown in FIG. 6 or long pants shown in FIG. 7.

It will be appreciated that the term hydrophobic and hydrophilic are comparative terms and depend upon selection of fibres and yarn with different surface tension, contact angle, shape of cross section, diameters of fibres, chemical and physical finishing, and so, forth. Thus, it will be understood that the terms "hydrophobic" and "hydrophilic" are used in the specification and claims as relative terms. This means that the composite textile fabric includes materials that are hydrophobic and hydrophilic relative to one another rather than necessarily having such properties in comparison to a norm or some industrial standard, for example.

We claim:

1. A composite textile fabric comprising a generally uniform single fabric layer consisting of a hydrophobic material and a hydrophilic material, the single fabric layer including an inner exposed surface of the hydrophobic and hydrophilic materials that is predominantly the hydrophobic material, and an outer surface of the hydrophobic and hydrophilic materials that is predominantly the hydrophilic material, the fabric providing a one-way liquid transport system, transporting liquid away from the inner surface towards the outer surface.

2. A composite fabric according to claim 1, in which the hydrophilic material is polypropylene.

3. A composite fabric according to claim 1, in which the hydrophilic material is one of polyester and cotton.

4. A diaper comprising an inner layer of a fabric comprising a generally uniform single fabric layer consisting of a hydrophobic material and hydrophilic material, the single fabric layer including an inner exposed surface of the hydrophobic and hydrophilic materials that is predominantly the hydrophobic material and an outer surface of the hydrophobic and hydrophilic materials that is predominantly the hydrophilic material, the fabric providing a one-way liquid transport system, transporting liquid away from the inner surface towards the outer surface, a middle layer of a treated cotton fabric, and an outer layer of a waterproof material.

5. An article of clothing including the composite textile fabric layer according to claim 1.

6. A mattress cover including a composite textile fabric layer according to claim 1.

7. The article of clothing according to claim 5 wherein the article of clothing is boxer shorts.

8. The article of clothing according to claim 5 wherein the article of clothing is long pants.

* * * * *